United States Patent [19]

Badie

[11] Patent Number: 5,250,075
[45] Date of Patent: Oct. 5, 1993

[54] BAYONET SUCKER FORCEPS

[76] Inventor: Behnam Badie, 11140 Rose Ave. #202, Los Angeles, Calif. 90034

[21] Appl. No.: 939,949

[22] Filed: Sep. 2, 1992

[51] Int. Cl.⁵ ............................................. A61B 17/32
[52] U.S. Cl. ................................... 606/207; 606/174; 604/35
[58] Field of Search ............... 606/51, 52, 205–211, 606/42, 34, 174; 128/750–755; 604/22, 118, 119, 35, 27; 433/99, 94, 95; 294/99.2

[56] References Cited

U.S. PATENT DOCUMENTS 3,980,086 9/1976 Kletschka et al. ............... 606/174
4,049,002 9/1977 Kletschka et al. ............... 606/174

FOREIGN PATENT DOCUMENTS 0932982 7/1963 United Kingdom ............... 606/207

Primary Examiner—C. Fred Rosenbaum
Assistant Examiner—William Lewis
Attorney, Agent, or Firm—Marger, Johnson, McCollom & Stolowitz

[57] ABSTRACT

Surgical forceps with integral suction are disclosed. The forceps include first and second elongated members movably interconnected so that the tips are juxtaposed for movement between spaced apart and clamping positions. One of the members has a channel extending from a suction orifice at the tip to a suction adapter, and a bypass port in the inward facing sidewall which admits ambient air to the channel. The other member has a suction control plug juxtaposed on its inward facing side for insertion into the bypass port to reduce the ambient air admitted to the channel. The forceps members are resiliently deformable and the suction control port and plug are arranged so that, with the forceps tips remaining in contact, the port is closed by compressing the members together and is opened by relaxing the compression. Movement of the elongated members into the clamping position using the same action as normally used with forceps, and then applying compression, controls suction through the suction orifice.

15 Claims, 4 Drawing Sheets

BAYONET SUCKER FORCEPS

BACKGROUND OF THE INVENTION

This invention relates generally to surgical instruments and more particularly to surgical forceps used in microscopic surgery having suction means for removing fluid and/or gases from a surgical area.

Surgical instruments having both grasping and suctioning capability are known in the art. The desirability and benefit of using a single instrument capable of manipulating the surgical area and aspirating fluids and/or gases away therefrom, has prompted the development of several such devices. For example, a tweezer-like configuration having a small conduit in one or both of the leg members capable of suctioning fluid and/or gases is described in U.S. Pat. No. 3,916,909 and further described in U.S. Pat. No. 4,096,864, both issued to Kletschka et al. In addition, bipolar forceps having one leg for providing suction are commercially available through Codman Inc., e.g., GREENWOOD Bipolar and Suction Forceps, Model 30-1525 and 1526.

These devices must also provide some means for controlling the suction produced by the device. The Codman bipolar and suction forceps (Model 30-1525 and 1526) provides no way to modulate the amount of suction produced by the device, other than decreasing the amount of suction produced by the source. Having the suction always on impairs the utility of the device to selectively remove debris from the surgical area as well as its effectiveness in grasping and releasing tissue. Kletschka et al. describes surgical forceps consisting of two legs, one or both legs having a conduit extending from the tip of the leg to a suction source, through which suctioned material is removed from the surgical site. A slot-like opening on the exterior wall of the leg exposes a porion of the conduit, thereby diverting the suction away from the tip to the opening when the opening is unobstructed. To transfer the suction to the tip of the leg requires the operator to obstruct the opening with a finger, or to move a slide member over the opening with a finger. This provides the surgeon with a variable control of the amount of suction.

Movement of the sort required by Kletschka et al. to operate the suction control causes the operator to change the natural position of the hand holding the instrument. This movement results in the momentary loss of control of the instrument during surgery. For extremely delicate surgery, such as neurological, vascular, and cardiothoracic microsurgery, the temporary loss of control of the device can have disastrous consequences, e.g., damage a nerve or blood vessel. Even in less critical situations, it is inconvenient and inefficient for the surgeon to have to change hand positions to switch between suctioning and using the instrument as a forceps. Consequently, surgical instruments requiring unnatural hand movements to control the suction, such as that required by Kletschka et al., have not achieved acceptance by surgeons.

Accordingly, a need remains for surgical forceps including means for suctioning fluid and/or gases away from the surgical area which can be controlled by the user without adversely affecting the surgical utility of the device.

SUMMARY OF THE INVENTION

It is, therefore, an object of the invention to provide improved manually controllable suction in combination with surgical forceps. A more specific object is to enable a surgeon to use the instrument interchangeably as a suction device and forceps with minimal additional manipulation over forceps alone. Another object is to control the amount of suction at the suction orifice without impairing the surgical functionality of the device.

The invention is a combination forceps-suction instrument having a suction control means disposed on the inward facing sides of the forceps which varies the amount of suction present at the suction orifice responsive to the position of the leg members of the forceps with respect to each other. In the preferred embodiment, the suction control means comprises a bypass port on the inward facing side of the first leg through which ambient air is admitted when the legs are spaced apart, and a suction control plug on the inward facing side of the second leg juxtaposed to the bypass port. The control plug modulates the flow of ambient air admitted through the bypass port to control suction at the suction orifice responsive to movement of the elongated members.

A significant advantage of this invention is that the surgeon actuates suction with the same motion as to use the instrument as forceps. The suction control means is preferably arranged to act in stages so that merely closing the forceps or grasping tissue between the forceps tips does not actuate suction but further compressing the legs of the forceps does actuate suction. Another advantage is that this structure is simpler and more economic to make and maintain than prior art instruments of similar purpose.

The foregoing and other objects, features and advantages of the invention will become more readily apparent from the following detailed description of a preferred embodiment of the invention which proceeds with reference to the accompanying drawings.

DETAILED DESCRIPTION

Figure 1A:
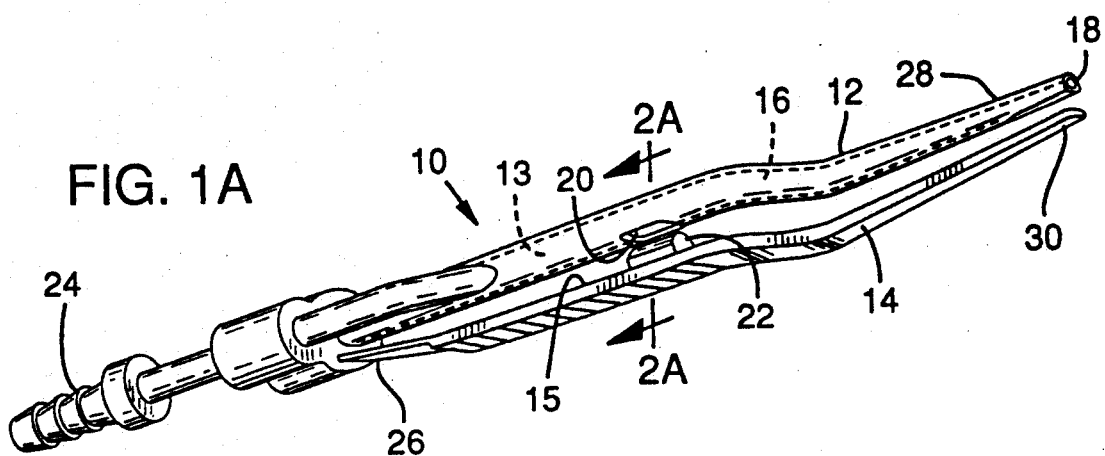
FIG. 1A is an oblique view of a surgical forceps of the bayonet type having means for controlling suction according to the invention disposed on the inward facing sides of the legs in a bypass position with the forceps legs spaced apart.

Referring to FIG. 1A, an oblique view of a surgical forceps 10, of the bayonet type, is shown which incorporates the suction control means 20,22 described herein and which is the object of the invention. Although bayonet-type forceps are shown, other types of forceps commonly used in neurological, vascular, and cardiothoracic surgery, e.g., bipolar forceps, clamping forceps, etc..., can also be used in conjunction with the inventive principles.

Figure 1B:
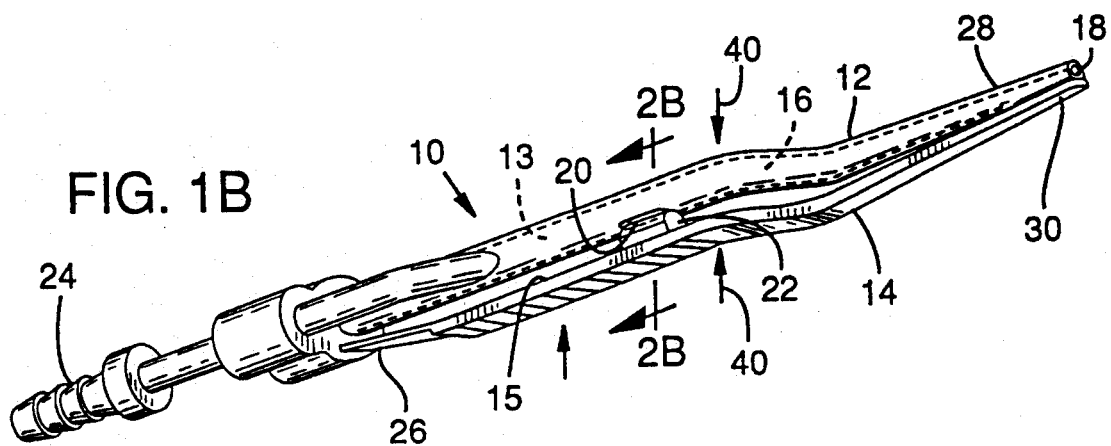
FIG. 1B is an oblique view of the surgical forceps of FIG. 1A having the means for controlling suction in a bypass position with the forceps legs close together.
Figure 1C:
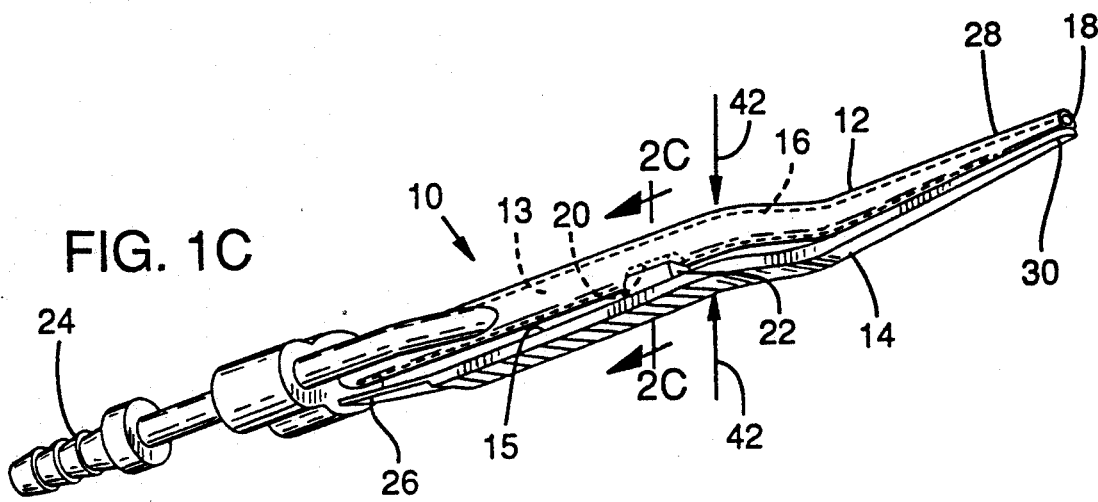
FIG. 1C is an oblique view of the surgical forceps of FIG. 1A having the means for controlling suction in a suctioning position with the forceps legs compressed together.

The bayonet forceps shown in FIGS. 1A-1C comprise two elongated members 12 and 14, hereafter referred to as legs, movably interconnected at a connecting point 26 at the rearward portion of the two legs. Each leg has an inward facing side 13,15 which defines a space between the two legs. For the bayonet forceps shown in FIGS. 1A-1C, one leg 14 has a longitudinally concave or bowed shape and is resiliently deformable, such that the leg can be flattened when compressed against leg 12 but returns to its original bowed position when no compressive force is applied to the legs. The invention applies equally as well to forceps having both legs concave and/or resiliently deformable.

The two legs are interconnected for movement between two distinct positions. In the first position, shown in FIG. 1A, the distal ends or tips 28 and 30 of the legs are spaced apart, and the second position, shown in FIG. 1C, the tips contact one another. The second position, shown in FIG. 1C, is hereafter referred to as the clamping position. There is also a third intermediate position, shown in FIG. 1B, in which the tips of the forceps are spaced close together but not contacting, e.g., 1 mm apart. This condition occurs when the surgeon to grasps tissue in the surgical area for manipulation. In an alternative embodiment, a more severe concave or bowed shape of the leg 14 would allow the tips to make contact in the third intermediate position.

The first leg 12 has a channel 16 extending within the leg from a suction orifice at the tip 18 to a suction adapter 24 at the rearward portion. The channel is the conduit through which the suctioned material is removed from the surgical site. The channel may extend the entire length of the leg, as shown in FIGS. 1A-1C, or it can extend along only a portion of the leg to wherever a suction adapter 24 is mounted on the leg.

Optionally, the second leg 14 can include a channel with an opening at its distal tip and a fitting at or along its proximal end for suction or for introducing an irrigation fluid. In this case, the irrigation channel can include a normally closed microvalve that is actuated by pressure to discharge irrigation fluid through the tip opening at the same time that suctioning is enabled via orifice 18.

Figure 3A:
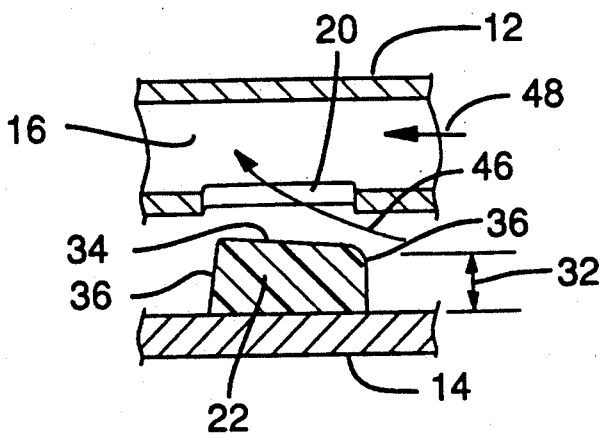
FIG. 3A is a longitudinal sectional view taken along lines 3A—3A in FIG. 2A.

On the inward facing side 13 of the first leg 12, spaced between the suction orifice 18 and the suction adapter 24, is a bypass port 20. This port opens the channel on the side 13 between the two legs for admitting ambient air to the channel. The opening 20 can take on a variety of shapes and sizes, e.g., rectangular, oval, circular, etc., dictated primarily by the dimensions of the leg and the amount of ambient air to be admitted through the opening. The size of the opening, relative to the size of the suction orifice, influences the amount of ambient air admitted to the channel through the suction orifice 18 when the legs are in the spaced apart position. FIG. 3A shows the admission of ambient air into the channel through the bypass port 46 and the air admitted through the suction orifice 18 when the legs are spaced apart. The amount of ambient air admitted to the channel through each opening is a function of the ratio of the areas of the two openings. Preferably, the bypass port opening 20 allows only such a limited amount of ambient air to be admitted through the suction orifice when the legs are spaced apart, indicated by the relative sizes of the arrows 46 and 48, that the suction produced at the suction orifice 18 is not sufficient to suck fluid or tissue.

The second leg 14 has a suction control plug 22 on the inward facing side 15 juxtaposed to the bypass port 20. The suction control plug 22 is positioned on the second leg to enter the bypass port when the legs are placed in the clamping position. In the preferred embodiment of the invention, the combination of suction control plug 22 and bypass port 20 is positioned so as not to obscure the surgeon's view of the forceps tips while operating under a microscope, i.e., spaced rearward from distal tips 28,30.

Figure 2A:
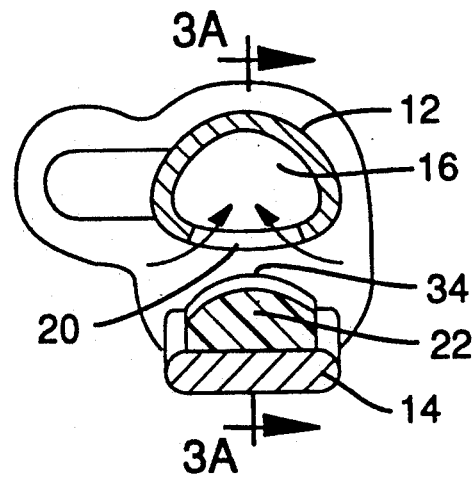
FIG. 2A is a cross-sectional view taken along lines 2A—2A in FIG. 1A.
Figure 2B:
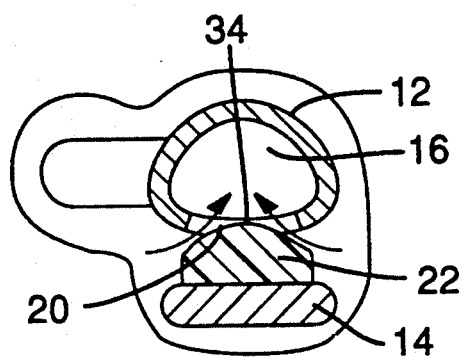
FIG. 2B is a cross-sectional view taken along lines 2B—2B in FIG. 1B.
Figure 2C:
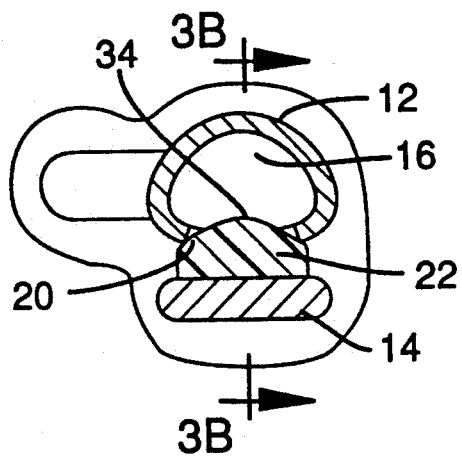
FIG. 2C is a cross-sectional view taken along lines 2C—2C in FIG. 1C.

The presence of the suction control plug 22 in the bypass port 20 reduces the amount of port area available for admitting ambient air. When in the intermediate position shown in FIG. 2B, the suction control plug only partially obstructs the bypass port, allowing some ambient air to continue to be admitted through the bypass port as shown in FIG. 2B. When the legs are in the clamping position, however, the suction control plug is inserted into the bypass plug as shown in FIG. 2C, thereby transferring suction from the bypass port 20 entirely to the suction orifice 18 as shown by arrow 50 in FIG. 3B.

Figure 3B:
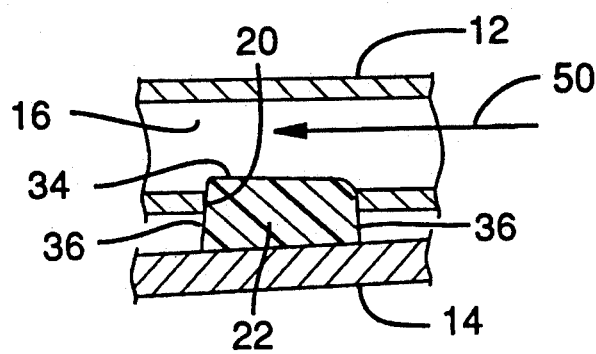
FIG. 3B is a longitudinal sectional view taken along lines 3B—3B in FIG. 2C.

The suction control plug 22 is sized according to the dimensions of the area defined by the bypass port and the width of the channel. The plug can be designed to precisely fit within the bypass port, as shown in FIG. 3B, thereby effectively eliminating all ambient air admitted through the bypass port. Or the plug can be sized to allow a predetermined amount of ambient air to be admitted through the bypass port when the plug is fully inserted. In the preferred embodiment, the plug 22 is rectangular, designed to fit precisely within corresponding rectangular dimensions of the bypass port. In addition, the stand-off height 32 of the plug, measured from the second leg as shown in FIG. 3A, is chosen so that when the plug is fully inserted into the bypass port, that portion 34 which enters the bypass port does not impede the passage of material through the channel.

In addition to varying the size of the plug, the shape of the plug can be altered to provide further controllability of the amount of ambient air admitted through the bypass port. The inner face 34 of the plug can either be parallel to the bypass port at the point of insertion, or it can be inclined relative to the bypass port. For the rectangular plug with a parallel face 34, the amount of ambient air admitted through the bypass port will have two distinct settings, depending on whether the plug is inserted or not. In the first setting, substantially all of the ambient air is admitted through the bypass port. In the second, substantially all of the ambient air is admitted through the bypass port.

By inclining the inner face 34 of the plug, the amount of bypass port area capable of admitting ambient air is more gradually reduced as the suction control plug is further inserted into the bypass port opening. The face of the plug can either be inclined towards the tips or away from the tips, or inclined towards one side of the leg or the other. In all cases, the amount of suction produced at the suction orifice is strictly a function of the spacing between the two legs. As the legs are brought together into the clamping position, suction is transferred from the bypass port to the suction orifice according to the size and shape of the plug.

Similarly, by tapering the sides 36 of the plug, the plug can be gradually inserted into the bypass port, resulting in incremental control of ambient air being admitted through both openings 18,20. The sides of the plug are tapered so that the portion of plug which first enters the port on insertion into the port is relatively smaller than subsequent portions of the plug that enter the port. One or more sides can be tapered in this manner, depending on the amount of variability the user requires. By tapering the sides of the plug, as the plug is inserted farther into the bypass port, the area of the bypass port capable of admitting ambient air is gradually reduced, providing the surgeon an additional degree of controllability of the suction by simply bringing the legs 12, 14 closer together.

Figure 4A:
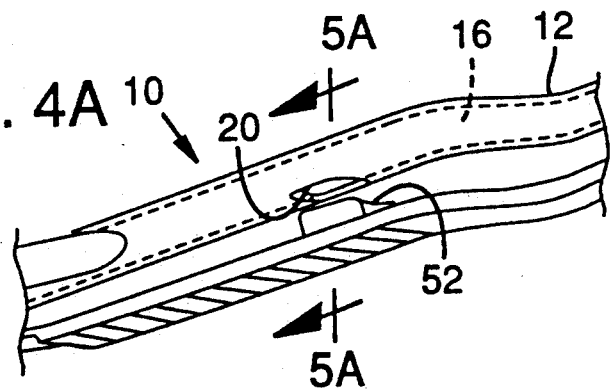
FIG. 4A is a perspective view of a section of the forceps shown in FIG. 1A having an alternative embodiment of the suction control plug in a bypass position with the legs in the spaced apart position.
Figure 4B:
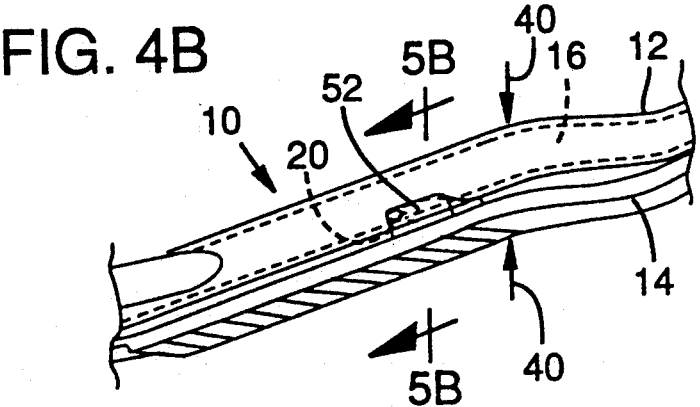
FIG. 4B is a perspective view similar to FIG. 4A showing the suction control plug in a suction position with the legs in the clamping position.
Figure 5A:
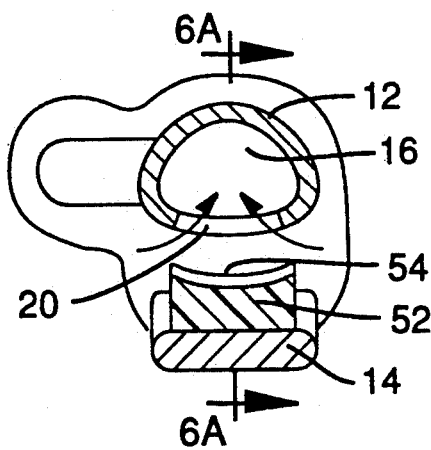
FIG. 5A is a cross-sectional view taken along lines 5A—5A in FIG. 4A.
Figure 5B:
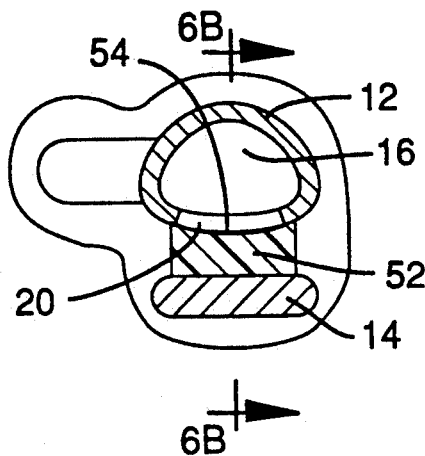
FIG. 5B is a cross-sectional view taken along lines 5B—5B in FIG. 4B.
Figure 6A:
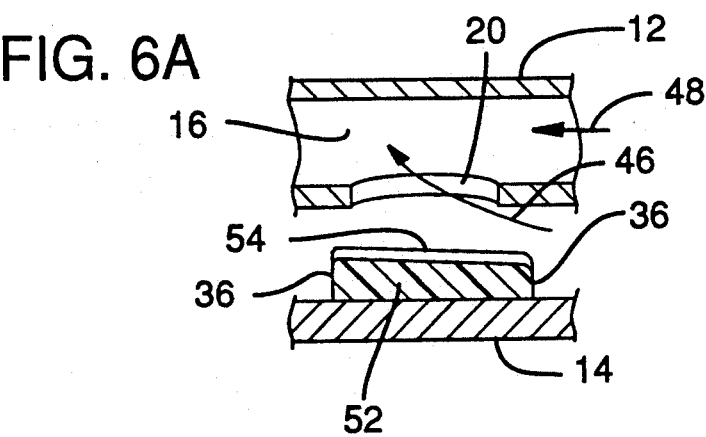
FIG. 6A is a longitudinal-sectional view taken along lines 6A—6A in FIG. 5A.
Figure 6B:
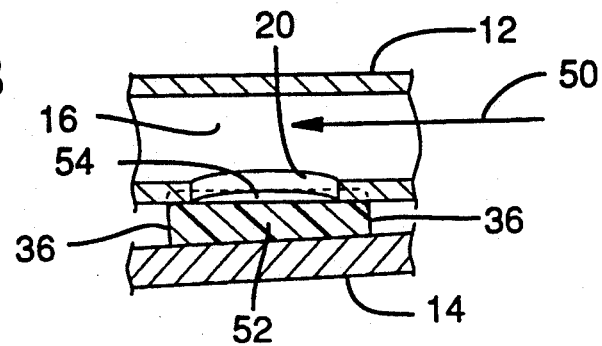
FIG. 6B is a cut-away cross-sectional view taken along lines 6B—6B in FIG. 5B.

An alternative embodiment of the suction control plug 52 is shown in FIGS. 4A and 4B, corresponding to leg positions shown FIGS. 1A and 1C. In this embodiment, the inner face 54 of the plug is shaped to the outer contour of the opposing leg member and is sized larger than the bypass port so that the inner face 54 envelops the bypass port when the two are brought together, as shown in FIG. 5B. A distinct advantage of this embodiment of the suction control plug 52 is that the suction control plug does not impede the passage of material through the channel when the legs are in the clamping position.

In operation, the forceps are held in the surgeon's hand with the thumb and forefinger by grasping the outward facing sides of the device between joint 26 and the tips 28 and 30. The force required to move the legs from the spaced apart position to the clamping position is provided by compressing the legs together between the opposed thumb and forefinger as indicated by arrows 42 in FIG. 1C. In the preferred embodiment of the invention, the legs 12, 14 are hingedly interconnected, or welded together at joint 26, but resiliently moveable, so that the tips can be brought together into the clamping position. The height 32 of suction control plug 22, or that portion which enters the bypass port, is short enough and legs 12, 14 are bowed outward so that the tips 28, 30 can be in the clamping position without causing the suction control plug to be fully inserted into the bypass port 20, as shown in FIG. 2B. By applying an intermediate amount of compressive force on the two legs, as indicated by arrows 40 in FIG. 1B, the surgeon is able to grasp tissue in the surgical area with the tips of the forceps free of suction at the suction orifice, the presence of which would compromise the ability of the device to grasp and manipulate in the surgical area. However, by applying additional compression to the legs, as indicated by arrows 42 in FIG. 1C, the legs are brought closer together engaging the suction control plug and the bypass port, thereby transferring suction to the suction orifice. The user can do this without changing the position of the thumb and forefinger on the device. In this manner, the surgical forceps sucker, as described herein, can be opened singlehandedly both as a surgical forceps and as a surgical sucker without requiring any unnatural hand movement to switch between the two. In addition, the bypass plug 52 shown in FIG. 4A and 4B can also produce similar suction control.

Besides those noted above, other variations can be made in the way the invention is implemented. For example, the suctioning structure can be arranged in forceps of the type having two members pivotally interconnected by a hinge or pivot pin, to form a scissors-like forceps. The suction orifice and channel suction coupling is connected to the handle of member. The suction control means 20, 22 can be built into the distal portions of members midway between hinge and tip. Alternatively, the suction control means can be built into the handle portions.

Having described and illustrated the principles of the invention in a preferred embodiment thereof, it should be apparent that the invention can be modified in arrangement and detail without departing from such principles. I claim all modifications and variation coming within the spirit and scope of the following claims.

I claim:

1. A surgical sucker forceps comprising:
    first and second elongated members each having a first end and a rearward portion and an inward facing side, each elongated member having a distal tip at the first end thereof;
    means for movably interconnecting the first member to the second member so that the tips are juxtaposed for movement between spaced apart and clamping positions;
    a channel extending within the first member from a suction orifice at the tip of the first member to a suction adapter;
    means defining a bypass port in a sidewall of the first member for admitting ambient air to the channel, the bypass port positioned on the inward facing side of the first member between the suction orifice and the suction adapter; and
    a suction control plug on the inward facing side of the second member juxtaposed to the bypass port for selectably obstructing the bypass port to reduce the ambient air admitted to the channel to control suction through the suction orifice when the tips of the elongated members are in the clamping position.

2. A surgical sucker forceps according to claim 1 wherein the first and second elongated members are resiliently deformable and the suction control plug and bypass port are arranged so that the plug blocks the port to commence suction when the members are compressed together and opens the port to cease suction when compression is relaxed.

3. A surgical sucker forceps according to claim 1 in which the suction control plug and bypass port are arranged so that the plug can block the port when the tips contact one another and the port is open to admit ambient air to the channel when the tips are spaced apart.

4. A surgical sucker forceps according to claim 1 wherein the suction control plug has a cross section which is substantially similar to the opening defined by the bypass port so that when the plug is fully inserted into the bypass port substantially all of the ambient air passing through the channel is admitted through the suction orifice.

5. A surgical sucker forceps according to claim 1 wherein the suction control plug has an inner face juxtaposed to the second leg, the inner face having an area greater than the area of the bypass port and a contour substantially similar to the opposing face of the second leg so that when the suction control plug comes into contact with the bypass port substantially all of the area defined by the bypass port is enclosed by the inner face of the suction control plug.

6. A surgical sucker forceps according to claim 1 wherein the suction control plug has a rectangular cross section taken along the inward facing side of the first member.

7. A surgical sucker forceps according to claim 6 wherein the means defining a bypass port comprises a rectangular opening substantially similar to the cross section of the suction control plug.

8. A surgical sucker forceps according to claim 1 wherein the suction control plug has a top surface facing the second member and which is substantially parallel to the inward facing side of the first member.

9. A surgical sucker forceps according to claim 1 wherein the suction control plug has an top surface facing the second member and which is inclined relative to the inward facing side of the first member.

10. A surgical sucker forceps according to claim 1 wherein the means defining a bypass port and the suction control plug are positioned nearer the rearward portion of the members than to the distal tips so that the plug does not obscure the surgeon's view when used under a microscope.

11. A surgical sucker forceps according to claim 1 wherein the first and second elongated members are resiliently interconnected.

12. A surgical sucker forceps according to claim 1 wherein the first and second elongated members are pivotally interconnected.

13. A surgical sucker forceps comprising:
 first and second elongated members each having a first end and a rearward portion and an inward facing side, each elongated member having a distal tip at the first end thereof;
 means for movably interconnecting the first member to the second member so that the tips are juxtaposed for movement between spaced apart and clamping positions;
 a channel extending within the first member from a suction orifice at the tip of the first member to a suction adapter;
 interengageable suction control means disposed on the inward facing sides of the first and second members for controlling suction from the suction orifice through the channel; and
 at least one of the first and second members being resiliently deformable when the tips are in contact so that compressing the members actuates to suction compression control means.

14. A method of controlling the suction produced by a surgical sucker forceps comprising:
 providing a forceps having movably interconnected first and second elongated members with distal tips juxtaposed for clamping action, the first member having a suction channel extending from a suction orifice at the tip to a suction adapter, and the first and second members having interengageable suction control means disposed on the inner faces;
 separating the first and second members at a first position so that their distal tips are spaced apart thereby disengaging the suction control means so that minimal suction is produced at the suction orifice; and
 moving the first and second members together to a second position so that their distal tips are in a clamping position so that the suction control means is engaged and suction is produced at the suction orifice.

15. A method of controlling the suction produced by a surgical sucker forceps according to claim 14 wherein the step of moving the first and second members together to the second position further comprises:
 moving the first and second members together so that their distal tips are in a noncompressed clamping position wherein the suction control means is disengaged and minimal suction is produced at the suction orifice; and
 moving the first and second members closer together to a compressed clamping position so that the suction control means is engaged and suction is produced at the suction orifice.

* * * * *